United States Patent [19]

Seitz

[11] 4,243,809

[45] Jan. 6, 1981

[54] PROCESS FOR THE PRODUCTION OF PYRIDONE COMPOUNDS

[75] Inventor: Karl Seitz, Oberwil, Switzerland

[73] Assignee: Ciba-Geigy Corporation, Ardsley, N.Y.

[21] Appl. No.: 954,820

[22] Filed: Oct. 26, 1978

[30] Foreign Application Priority Data

Nov. 4, 1977 [LU] Luxembourg .............................. 78454

[51] Int. Cl.³ .................... C07D 213/81; C07D 213/71
[52] U.S. Cl. .................................... 546/291; 546/193; 546/194; 546/261; 546/273; 546/280; 546/281; 546/283; 546/294; 544/131; 544/360; 260/156
[58] Field of Search ............... 546/294, 288, 291, 193, 546/194, 261, 273, 280, 281, 283; 544/131, 360

[56] References Cited

U.S. PATENT DOCUMENTS 3,912,745  10/1975  Heinrich et al. ...................... 546/294

FOREIGN PATENT DOCUMENTS 1956142  6/1970  Fed. Rep. of Germany ........... 546/294

Primary Examiner—Henry R. Jiles
Assistant Examiner—Natalia Harkaway
Attorney, Agent, or Firm—Prabodh I. Almaula; Edward McC. Roberts

[57] ABSTRACT

The invention provides compounds of the formula

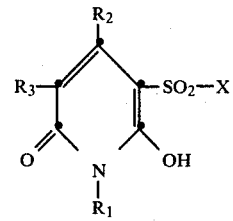

wherein each of $R_1$ and $R_2$ independently is a hydrogen atom or a substituted or unsubstituted alkyl or aryl radical, $R_3$ is a hydrogen atom or the carbamoyl radical, and X is a substituted or unsubstituted alkyl or alkenyl radical. A process for preparing these compounds is also disclosed.

5 Claims, No Drawings

PROCESS FOR THE PRODUCTION OF PYRIDONE COMPOUNDS

The present invention relates to the formula

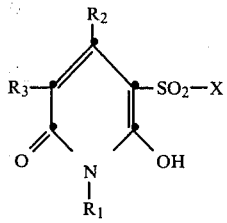

(1)

wherein each of $R_1$ and $R_2$ independently is a hydrogen atom or a substituted or unsubstituted alkyl or aryl radical, $R_3$ is a hydrogen atom or the carbamoyl radical, and X is a substituted or unsubstituted alkyl or alkenyl radical.

Alkyl radicals $R_1$ and $R_2$ can be saturated or unsaturated, linear, branched or cyclic. Examples of eligible substituents at the alkyl radicals are: halogen, cyano, thiociano, nitro, carbamoyl, sulfamoyl, carboxyl, sulfo, hydroxyl, —$NH_2$, N-alkylamino, N,N-dialkylamino, N-monoalkylcarbamoyl, N,N-dialkylcarbamoyl, N-phenylcarbamoyl, alkoxy, alkoxycarbonyl, cyanoalkoxy, acyloxy, acyl, acylamino, phenyl, naphthyl, phenoxy, naphthoxy, and heterocyclic radicals, such as the furane, thiophene or thiazole radical etc.

Eligible aryl radicals $R_1$ and $R_2$ are: phenyl, naphthyl or the radical of diphenyl or stilbene. The aryl radicals can be further substituted, for example by the substituents recited above in respect of $R_1$ and $R_2$ as alkyl radicals.

Examples of substituted or unsubstituted alkyl or aryl radicals $R_1$ and $R_2$ are: methyl, ethyl, propyl, isopropyl, butyl, isobutyl, sec-butyl, tert-butyl, hexyl, octyl, octadecyl, cyclohexyl, 2-methylcyclohexyl, vinyl, allyl, β-chloroethyl, β-bromoethyl, cyanomethyl, β-cyanoethyl, N-methylaminocarbonylmethyl, N-ethylaminocarbonylmethyl, β-N,N-dimethylaminocarbonylethyl, β-N-propylaminocarbonylethyl, β-N,N-diethylaminocarbonylethyl, γ-N-ethoxypropylaminocarbonylmethyl, γ-N-hexyloxypropylaminocarbonylmethyl, γ-carbamoylpropyl, β-hydroxyethyl, γ-hydroxypropyl, β,γ-dihydroxypropyl, β-hydroxyphenethyl, β-aminoethyl, γ-aminopropyl, 6-amino-hexyl, β-N,N-dimethylaminoethyl, β-N,N-diethylaminoethyl, β-isopropylaminoethyl, β-N,N-dipropylaminoethyl, γ-N,N-dimethylaminopropyl, γ-N,N-diethylaminopropyl, γ-(β-hydroxyethylamino)-propyl, methoxymethyl, β-methoxyethyl, γ-methoxypropyl, β-ethoxyethyl, γ-ethoxypropyl, β-propyloxyethyl, γ-hexyloxypropyl, γ-isopropyloxypropyl, γ-cyclohexyloxypropyl, methoxycarbonylmethyl, ethoxycarbonylmethyl, β-propyloxycarbonylethyl, γ-methoxycarbonylpropyl, γ-ethoxycarbonylpropyl, β-(β-cyanoethoxy)-ethyl, acetyloxymethyl, β-acetyloxyethyl, β-cyanacetyloxyethyl, β-butyryloxyethyl, γ-methoxyacetyloxypropyl, β-benzoyloxyethyl, acetylmethyl, β-acetylethyl, β-benzoylethyl, β-acetylaminoethyl, β-benzoylaminoethyl, benzyl, phenethyl, phenoxyethyl, phenthioethyl, β-methoxycarbonylethylcarbonyl-β-oxyethyl, β-benzyloxyethyl, β-butylaminocarbonyloxyethyl, β-ethoxycarbonyloxyethyl, β-phenethyloxyethyl, β-phenylaminocarbonyloxyethyl, β-phenoxycarbonylethyl, β-phenoxycarbonyloxyethyl, β-phenylacetyloxyethyl, β-phenoxyacetyloxyethyl, β-phenylsulfonylethyl, β-phenylsulfonyloxyethyl, β-phenylthioethyl, β-4-methoxycarbonyl-benzoyloxyethyl, β-3-methylbenzoyloxy-ethyl, β-4-methoxy-benzoyloxy-ethyl, β-4-chlorobenzoyloxy-ethyl, β-methylsulfonylaminoethyl, γ-di-(β-hydroxyethyl)amino-propyl, β-pyridyl-(3)-carbonyloxy-ethyl, furyl-(2)-methyl, tetrahydrofuryl-(2)-methyl, thiazolyl-(2)-methyl, 1,3-thiazolinyl-(2)-methyl, 3-indolylmethyl, pyridyl-(2)-methyl, pyridyl-(4)-methyl, β-pyridyl-(2)-ethyl, piperidyl-(2)-methyl, 3-piperidyl-(1)-ethyl, β-piperidyl-(2)-ethyl, β-piperidyl-(4)-ethyl, β-piperazinyl-(1)-ethyl, β-morpholinyl-(4)-ethyl, β-pyrrolidinyl-(1)-ethyl, phenyl, 3-methylphenyl, 4-methoxyphenyl, 4-methylthiophenyl, 4-chlorophenyl, 4-aminophenyl.

Suitable alkyl radicals X are straight chain or branched alkyl radicals, for example methyl, ethyl, propyl, n-butyl, isopropyl. The radical X can be further substituted and is in particular an alkyl radical which can be substituted by halogen, alkoxy or aryl. In this preferred embodiment, eligible substituents are respectively: fluorine, chlorine, bromine; alkoxy groups of 1 to 12 carbon atoms which can be straight chain or branched; phenyl and naphthyl. Examples of unsubstituted radicals X are: methyl, ethyl, propyl, isopropyl, butyl, isobutyl, sec-butyl, tert-butyl, n-hexyl, cyclohexyl, vinyl, allyl. Examples of substituted radicals X are: chloromethyl, β-chloroethyl, trifluoromethyl, perfluoro-n-butyl, $C_1$–$C_{12}$-alkoxymethyl, benzyl, phenethyl.

Preferably, X is low molecular alkyl, by which are meant alkyl radicals of 1 to 6, especially 1 to 4, carbon atoms.

Preferred compounds are those of the formula I wherein $R_1$ is a hydrogen atom or an alkyl radical of 1 to 4 carbon atoms, $R_2$ is an alkyl radical of 1 to 4 carbon atoms, $R_3$ is a hydrogen atom or the carbamoyl radical, and X is an alkyl radical of 1 to 4 carbon atoms.

A particularly valuable compound falling within this subgroup is that of the formula

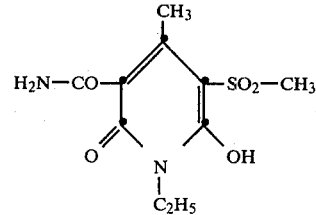

(2).

The compounds of the formula (1) are obtained by reacting compounds of the formula

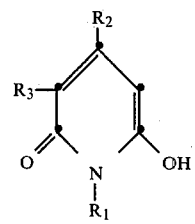

(3)

wherein $R_1$, $R_2$ and $R_3$ are as defined in formula (1), in an aqueous alkaline medium, with compounds of the formula $$Y\text{-}SO_2\text{-}X \quad (4)$$

wherein X is as defined in formula (1) and Y is a halogen atom.

The starting materials are preferably compounds of the formulae (3) and (4) wherein $R_1$ is a hydrogen atom or an alkyl radical of 1 to 4 carbon atoms, $R_2$ is an alkyl radical of 1 to 4 carbon atoms, $R_3$ is a hydrogen atom or the carbamoyl radical, X is an alkyl radical of 1 to 4 carbon atoms and Y is a halogen atom. A halogen atom Y is a fluorine, chlorine or bromine atom.

The above compound of the formula (2) is obtained by reaction of a compound of the formula

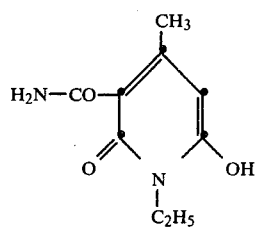
(5)

with methanesulfonyl chloride of the formula $$Cl\text{-}SO_2\text{-}CH_3 \quad (6)$$

in an aqueous alkaline medium.

The reaction of the invention is preferably carried out in aqueous medium; however, it can also be carried out in an organic solvent, in a mixture of organic solvents, or in a mixture of water and one or more organic solvents.

Suitable organic solvents for the reaction are: dimethyl formamide, dimethyl sulfoxide, acetic acid and pyridine. The reaction can furthermore be carried out in a solvent two-phase system. A suitable system of this kind is water/organic solvent, for example water/methylene chloride or water/toluene.

The reaction is carried out in an alkaline medium. A suitable pH range for this medium is between 8 and 14. The reaction is preferably carried out in a pH range between 11 and 12.

The conventional alkalies are employed, such as hydroxides, carbonates, bicarbonates or acetates of alkali metals or alkaline earth metals, or organic bases, such as tertiary amines, for example triethylamine, or heterocyclic nitrogen compounds, such as pyridine etc.

In a preferred embodiment, the reaction of the present invention is carried out in a strongly alkaline aqueous solution, using in particular sodium hydroxide as alkali.

In general the reaction is carried out in the temperature range between 0° and 100° C. Preferably a low temperature is chosen, for example between 0° and 20° C.

When the reaction is complete, the compounds of the formula (1) can be salted out, for example by addition of sodium chloride. The compound of the formula (1) is then obtained in the form of the monosodium salt. This salt is dissolved in water and then concentrated hydrochloric acid or sulfuric acid is added to the solution, whereupon the free acid precipitates and can be isolated.

The following compounds may be cited as starting compounds of the formula (3):

3-carbamoyl-4-ethyl-2,6-dihydroxy-pyridine,
1-ethyl-3-carbamoyl-4-methyl-6-hydroxy-pyridone-(2),
1,4-dimethyl-3-carbamoyl-6-hydroxy-pyridone-(2),
3-carbamoyl-4-methyl-2,6-dihydroxy-pyridine,
1-cyclohexyl-3-carbamoyl-4-methyl-6-hydroxy-pyridone-(2),
1-n-propyl-3-carbamoyl-4-methyl-6-hydroxy-pyridone-(2),
1-ethyl-3-carbamoyl-4-(4'-methoxy-3'-sulfophenyl)-6-hydroxy-pyridone-(2),
1-β-aminoethyl-4-methyl-6-hydroxy-pyridone-(2),
1-phenyl-3-carbamoyl-4-methyl-6-hydroxy-pyridone-(2),
1-β-hydroxyethyl-4-methyl-6-hydroxy-pyridone-(2),
1-isopropyl-3-carbamoyl-4-methyl-6-hydroxy-pyridone-(2),
1-ethyl-3-carbamoyl-4-sulfomethyl-6-hydroxy-pyridone-(2),
1-phenyl-4-methyl-6-hydroxy-pyridone-(2),
4-methyl-2,6-dihydroxy-pyridine,
1-ethyl-4-methyl-6-hydroxy-pyridone-(2),
4-sulfomethyl-2,6-dihydroxy-pyridine,
4-methyl-6-hydroxy-pyridone-(2),
1-ethyl-4-phenyl-6-hydroxy-pyridone-(2),
1-n-butyl-3-carbamoyl-4-methyl-6-hydroxy-pyridone-(2),
1-γ-isopropoxypropyl-4-methoxymethyl-6-hydroxy-pyridone-(2).

The following compounds may be cited as starting compounds of the formula (4):
methanesulfonyl chloride,
chloromethanesulfonyl chloride,
trichloromethanesulfonyl chloride,
ethanesulfonyl chloride,
2-chloroethanesulfonyl chloride,
vinylsulfonyl chloride,
vinylsulfonyl fluoride,
3-chloropropanesulfonyl chloride,
1-chlorobutane-3-sulfonyl chloride,
1-chlorobutane-4-sulfonyl chloride,
allylsulfonyl chloride,
benzylsulfonyl chloride,
4-nitrobenzylsulfonyl chloride,
methanesulfonyl bromide,
methanesulfonyl fluoride,
bromomethanesulfonyl bromide,
ethanesulfonyl bromide,
ethanesulfonyl fluoride,
2-bromoethanesulfonyl bromide,
2-perfluorobutylsulfonyl fluoride.

The compounds of the formula (1) are new. They are valuable intermediates which can be used as coupling components for the production of azo dyes. If $R_3$ in formula (1) is the carbamoyl radical, it is split off during the coupling.

The compounds of the formula (1) can exist in several tautomeric forms. To simplify the description, the compounds are illustrated in the formulae in only one of these tautomeric forms. However, it must be expressly emphasised, that, throughout this specification, especially in the claims, the description always refers to compounds in any one of these tautomeric forms.

The invention is illustrated by the following Examples, in which the parts are by weight, unless otherwise stated.

EXAMPLE 1

78.5 parts of 1-ethyl-3-carbamoyl-4-methyl-6-hydroxypyridone-(2) are suspended in 1000 parts of water and the pH of the suspension is adjusted to 12 with 10 N sodium hydroxide solution. The resulting clear solution is cooled to about 5° C. Then 92 parts of methanesulfonyl chloride are added dropwise at 5° to 10° C. in the course of 1 hour, while keeping the pH of the reaction mixture at 12 by the simultaneous addition of 10 N sodium hydroxide solution. The ice cooling is then removed and the reaction mixture is kept for 3 to 5 hours at room temperature. The reaction product is salted out from the clear solution by addition of 20% by volume of sodium chloride, collected by filtration and washed with sodium chloride solution.

For further purification, the crude product is dissolved in 1000 parts of water and salted out once more by addition of 200 parts of sodium chloride. It is collected by filtration and dried in vacuo at 80° C. affording about 80 parts of the monosodium salt of 1-ethyl-3-carbamoyl-4-methyl-5-methylsulfonyl-6-hydroxypyridone-(2) in the form of a white powder.

| $C_{10}H_{13}N_2O_5SNa$ (mol.wt. 296) | |
| --- | --- |
| calculated: | found: |
| 40.6% C | 39.6% C |
| 4.4% H | 4.4% H |
| 9.5% N | 9.4% N |
| 10.8% S | 10.6% S |

By acidifying an aqueous solution of the sodium salt with hydrochloric acid, the free acid can then be isolated in the form of fine needles. After recrystallisation from water, the product melts at 169°–170° C.

| $C_{10}H_{14}N_2O_5S$ (mol.wt. 274) | |
| --- | --- |
| calculated: | found: |
| 43.8% C | 43.9% C |
| 5.2% H | 5.2% H |
| 10.2% N | 10.2% N |
| 11.7% S | 12.2% S |

EXAMPLE 2

50 parts of 4-methyl-2,6-dihydroxypyridine are suspended in 800 parts of water and the pH value of the suspension is adjusted to 12 with 40 parts of 10 N sodium hydroxide solution. The resulting clear solution is cooled to 0°–5° C., then 400 parts of ice are added and 50.4 parts of methanesulfonylchloride are added dropwise at 0° to 5° C. in the course of 1 hour, while keeping the pH of the reaction mixture is between 11.5 and 12 by the simultaneous addition of 10N sodium hydroxide solution. The reaction mixture is stirred for a further 1 hour and then filtered clear. The desired reaction product is isolated from the filtrate by addition of 500 parts of sodium chloride.

For further purification, the crude product is recrystallised from a 15% sodium chloride solution. The product is then collected by filtration and dried in vacuo at 90°–100° C., affording about 40 parts of the sodium salt of 4-methyl-5-methylsulfonyl-2,6-dihydroxypyridine in the form of colourless needles.

| $C_7H_8NO_4SNa$ (mol.wt. 225) | |
| --- | --- |
| calculated: | found: |
| 37.3% C | 36.1% C |
| 3.6% H | 3.5.% H |
| 6.2% N | 6.1% N |
| 14.2% S | 13.7% S |

EXAMPLE 3

44.8 parts of 1-n-butyl-3-carbamoyl-4-methyl-6-hydroxypyridone-(2) are suspended in 500 parts of water and the pH of the suspension is adjusted to 12 with 10 N sodium hydroxide solution. The resulting clear solution is cooled to 5° C. Then 46 parts of methanesulfonyl chloride are added dropwise at 5° to 10° C. in the course of 1 hour, while keeping the pH of the reaction mixture at 12 by the simultaneous addition of 10 N sodium hydroxide solution. The ice cooling is subsequently removed and the reaction mixture is kept for 3 hours at room temperature. The clear solution is acidified with 20 parts of 10 N hydrochloric acid. The precipitated 1-n-butyl-3-carbomyl-4-methyl-5-methylsulfonyl-6-hydroxypyridone-(2) is collected by filtration and recrystallised from water. Melting point: 152° C.

| $C_{12}H_{18}N_2O_5S$ (mol.wt. 302) | |
| --- | --- |
| calculated: | found: |
| 47.7% C | 47.8% C |
| 6.0% H | 6.0% H |
| 9.3% N | 9.2% N |
| 10.6% S | 10.6% S |

EXAMPLE 4

25.4 parts of 1-aminobenzene-3-cyclohexyl-sulfamide are dissolved in 300 parts of water with the addition of 22 parts by volume of conc. hydrochloric acid The solution is cooled with ice to 0° C. and diazotised at 0°–5° C. with 25 parts by volume of 4 N sodium nitrite. Any slight excess of nitrous acid is destroyed with sulfamic acid. The resulting suspension is then stirred into a solution of 33.3 parts of 1-γ-iso-propoxyproyl-4-methoxymethyl-5-methylsulfonyl-6-hydroxypyridone-(2) and 4 parts of sodium hydroxide in 400 parts by volume of water. After brief stirring the coupling is complete, and the completely precipitated dye is isolated by filtration, washed with water and dried. It is a yellow powder which dissolves in acetone to give a light yellow solution and in sulfuric acid to give a reddish yellow solution, and which dyes acetate rayon in the spinning solution/melt in a greenish yellow shade of good fastness properties. The dye has the formula

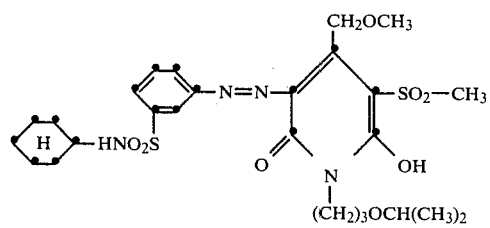

What is claimed is:

1. A process for the production of a compound of the formula

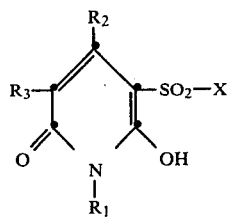

wherein $R_1$ is hydrogen, alkyl of 1 to 4 carbon atoms, aminoethyl, hydroxyethyl, isopropyloxypropyl, cyclohexyl or phenyl; $R_2$ is hydrogen, alkyl of 1 to 4 carbon atoms, methoxymethyl, sulfomethyl or phenyl unsubstituted or substituted by sulfo and methoxy;

$R_3$ is hydrogen or carbamoyl; and

X is alkyl of 1 to 6 carbon atoms which is unsubstituted or substituted by fluoro, chloro, bromo, alkoxy of 1 to 12 carbon atoms, phenyl or naphthyl; or is cyclohexyl, vinyl or allyl; which comprises reacting a compound of the formula

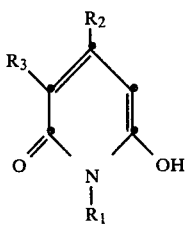

in a medium consisting of an aqueous alkaline medium having a pH of 8 to 14, with a compound of the formula

Y-SO₂-X where Y is fluoro, chloro or bromo.

2. A process according to claim 1, wherein $R_1$ is hydrogen or alkyl of 1 to 4 carbon atoms and $R_2$ is alkyl of 1 to 4 carbon atoms.

3. A process according to claim 1 wherein $R_1$ is hydrogen, ethyl or butyl, $R_2$ is methyl, $R_3$ is hydrogen or carbamoyl, X is methyl and Y is chlorine.

4. A process according to claim 3 wherein a compound of the formula

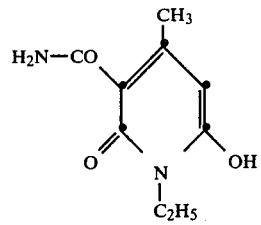

is reacted with methanesulfonyl chloride of the formula

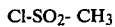

in an aqueous alkaline medium, to provide the compound of the formula

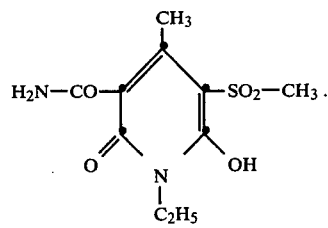

5. A process according to claim 4 wherein the reaction is carried out in an aqueous alkaline medium at a pH value of 11 to 12.

* * * * *